United States Patent [19]
Irie

[11] Patent Number: 5,419,904
[45] Date of Patent: May 30, 1995

[54] HUMAN B-LYMPHOBLASTOID CELL LINE SECRETING ANTI-GANGLIOSIDE ANTIBODY

[75] Inventor: Reiko F. Irie, Los Angeles, Calif.

[73] Assignee: The Regents of the University of California, Oakland, Calif.

[21] Appl. No.: 26,320

[22] Filed: Feb. 26, 1993

Related U.S. Application Data

[63] Continuation-in-part of Ser. No. 609,803, Nov. 5, 1990, abandoned.

[51] Int. Cl.$^6$ .................. A61K 39/395; C12N 5/22; C07K 16/18; C07K 16/30
[52] U.S. Cl. .................. 424/155.1; 424/142.1; 424/174.1; 435/240.26; 530/387.1; 530/387.7; 530/387.9; 530/388.15; 530/388.8
[58] Field of Search ............. 530/387.7, 387.9, 388.22, 530/388.8, 388.15; 424/85.8, 142.1, 174.1, 155.1; 435/240.26

[56] References Cited

U.S. PATENT DOCUMENTS

4,699,880 10/1987 Goldstein .................. 435/172.2
5,208,146 5/1993 Irie ........................ 435/7.23

OTHER PUBLICATIONS

Matsuki, T., et al., Proc. Ann Meeting Am Assoc Cancer Res, 29:A1694, 1988.
Hellstrom, I et al., Accomplishments in Cancer Res., pp. 216–240, 1984.
Morrison, S. L., et al, PNAS, 81:6851–6855, Nov. 1984.
Harris, W. J. et al., TIBTECH, 11:42–44, Feb. 1993.
Waldmann, T. A., Science, 252:1657–1662, Jun. 1991.
Furukawa, et al., J. Biol Chem 263(34):18507–18512, 1988.

*Primary Examiner*—David L. Lacey
*Assistant Examiner*—Susan A. Loring
*Attorney, Agent, or Firm*—Poms, Smith, Lande & Rose

[57] ABSTRACT

A human B-lymphoblastoid cell line which is identified as L612. The L612 cell line is an Epstein-Barr virus transformed cell line which secretes a human monoclonal antibody (L612) which is reactive with glycoconjugates having an epitope of terminal NeuAc α2-3 Galactose residue such as GM3 and GM4 present on a variety of human tumor tissues. The L612 antibody is useful in treating patients with the epitope containing tumors and is also useful in raising anti-id antibodies for use as surrogate antigens and diagnostic reagents.

13 Claims, 2 Drawing Sheets

```
      -19              -15                -10                  -5
  Met Glu Phe Gly Leu Thr Trp Leu Phe Leu Val Ala Asn Leu Lys
  ATG GAG TTT GGG CTG ACC TGG CTT TTT CTT GTG GCT AAT TTA AAA 1                   5                   10
  Gly Val Gln Cys Glu Val Gln Leu Leu Asp Ser Gly Gly Gly Leu
  GGT GTC CAG TGT GAG GTG CAG CTG TTG GAT TCT GGG GGA GGC TTG 15                  20                  25
  Val Gln Pro Gly Gly Leu Arg Leu Ser Cys Ala Ala Ser Gly
  GTA CAG CCT GGG GGG TGC CTG AGA CTC TCC TGT GCA GCC TCT GGA 30                  35                  40
  Phe Thr Phe Ser Ser Cys Ala Met Ser Trp Val Arg Gln Ala Pro
  TTC ACC TTT AGC AGC TGT GCC ATG AGC TGG GTC CGC CAG GCT CCA 45           50    52 52a           55
  Gly Lys Gly Leu Glu Trp Val Ser Ala Ile Ser Gly Ser Gly Gly
  GGG AAG GGG CTG GAG TGG GTC TCA GCT ATT AGT GGT AGT GGT GGT 60                  65                  70
  Ser Thr Tyr Tyr Ala Asp Ser Val Lys Gly Arg Phe Thr Ile Ser
  AGC ACA TAC TAC GCA GAC TCC GTG AAG GGC CGG TTC ACC ATC TCC 75                  80    82 82a 82b 82c
  Arg Asp Lys Ser Lys Asn Thr Leu Tyr Leu Gln Met Asn Ser Leu
  AGA GAC AAA TCC AAG AAC ACG TTG TAT CTG CAA ATG AAC AGC CTG 85                  90                  95
  Arg Ala Glu Asp Thr Ala Val Tyr Tyr Cys Ala Lys Gly Gly Asn
  AGA GCC GAG GAC ACG GCC GTA TAT TAC TGT GCG AAA GGT GGC AAC

100 A  B  C                105
  Asp Ile Leu Thr Gly Tyr Tyr Ala Trp Gly Gln Gly Thr Leu Val
  GAT ATT TTG ACT GGT TAT TAT GCT TGG GGC CAG GGA ACC CTG GTC 110                115
  Thr Val Ser Ser Gly Ser Ala Ser Ala
  ACC GTC TCC TCA GGG AGT GCA TCC GCC
```

Nucleotide and deduced amino acid sequence of the heavy chain of HuMab L612. Underlined amino acids represent the complementary determining regions CDR1, CDR2 and CDR3 in order.

```
  1
  Asp Ile Val Met 5                  10                 15
  Thr Gln Ser Pro Asp Ser Leu Ala Val Ser Leu Gly Glu Arg Ala
  ACC CAG TCT CCA GAC TCC CTG GCT GTG TCT CTG GGC GAG AGG GCC 20           25   27 27a 27b 27c 27d 27e 27f
  Thr Ile Asn Cys Lys Ser Ser Gln Ser Val Leu Tyr Ser Ser Asn
  ACC ATC AAC TGC AAG TCC AGC CAG AGT GTT TTA TAC AGC TCC AAC 30                  35                  40
  Asn Lys Asn Tyr Leu Ala Trp Tyr Gln Gln Lys Pro Gly Gln Pro
  AAT AAG AAC TAC TTA GCT TGG TAC CAG CAG AAA CCA GGA CAG CCT 45                  50                  55
  Pro Lys Leu Leu Ile Tyr Trp Ala Ser Thr Arg Glu Ser Gly Val
  CCT AAG CTG CTC ATT TAC TGG GCA TCT ACC CGG GAA TCC GGG GTC 60                  65                  70
  Pro Asp Arg Phe Ser Gly Ser Gly Ser Gly Thr Asp Phe Thr Leu
  CCT GAC CGA TTC AGT GGC AGC GGG TCT GGG ACA GAT TTC ACT CTC 75                  80                  85
  Thr Ile Ser Ser Leu Gln Ala Glu Asp Val Ala Val Tyr Tyr Cys
  ACC ATC AGC AGC CTG CAG GCT GAA GAT GTG GCA GTT TAT TAC TGT 90                  95                 100
  Gln Gln Tyr Tyr Ser Thr Pro Pro Thr Phe Gly Gln Gly Thr Lys
  CAG CAA TAT TAT AGT ACT CCT CCG ACG TTC GGC CAA GGG ACC AAG 105                110
  Val Glu Ile Lys Arg Thr Val Ala Ala Pro Ser Val Phe Ile Phe
  GTG GAA ATC AAA CGA ACT GTG GCT GCA CCA TCT GTC TTC ATC TTC
```

Nucleotide and deduced amino acid sequence of the light chain of HuMab L612. Underlined amino acids represent the complementary determining regions CDR1, CDR2, and CDR3 in order.

```
        -19                 -15                      -10                       -5
Met Glu Phe Gly Leu Thr Trp Leu Phe Leu Val Ala Asn Leu Lys
ATG GAG TTT GGG CTG ACC TGG CTT TTT CTT GTG GCT AAT TTA AAA 1                  5                          10
Gly Val Gln Cys Glu Val Gln Leu Leu Asp Ser Gly Gly Gly Leu
GGT GTC CAG TGT GAG GTG CAG CTG TTG GAT TCT GGG GGA GGC TTG 15                      20                       25
Val Gln Pro Gly Gly Cys Leu Arg Leu Ser Cys Ala Ala Ser Gly
GTA CAG CCT GGG GGG TGC CTG AGA CTC TCC TGT GCA GCC TCT GGA 30                      35                      40
Phe Thr Phe Ser Ser Cys Ala Met Ser Trp Val Arg Gln Ala Pro
TTC ACC TTT AGC AGC TGT GCC ATG AGC TGG GTC CGC CAG GCT CCA 45                      50    52 52a             55
Gly Lys Gly Leu Glu Trp Val Ser Ala Ile Ser Gly Ser Gly Gly
GGG AAG GGG CTG GAG TGG GTC TCA GCT ATT AGT GGT AGT GGT GGT 60                      65                      70
Ser Thr Tyr Tyr Ala Asp Ser Val Lys Gly Arg Phe Thr Ile Ser
AGC ACA TAC TAC GCA GAC TCC GTG AAG GGC CGG TTC ACC ATC TCC 75                      80    82 82a 82b 82c
Arg Asp Lys Ser Lys Asn Thr Leu Tyr Leu Gln Met Asn Ser Leu
AGA GAC AAA TCC AAG AAC ACG TTG TAT CTG CAA ATG AAC AGC CTG 85                      90                      95
Arg Ala Glu Asp Thr Ala Val Tyr Tyr Cys Ala Lys Gly Gly Asn
AGA GCC GAG GAC ACG GCC GTA TAT TAC TGT GCG AAA GGT GGC AAC

100 A   B   C                   105
Asp Ile Leu Thr Gly Tyr Tyr Ala Trp Gly Gln Gly Thr Leu Val
GAT ATT TTG ACT GGT TAT TAT GCT TGG GGC CAG GGA ACC CTG GTC 110                 115
Thr Val Ser Ser Gly Ser Ala Ser Ala
ACC GTC TCC TCA GGG AGT GCA TCC GCC
```

Nucleotide and deduced amino acid sequence of the heavy chain of HuMab L612. Underlined amino acids represent the complementary determining regions CDR1, CDR2 and CDR3 in order.

FIG. 1

```
1
Asp Ile Val Met 5                        10                         15
Thr Gln Ser Pro Asp Ser Leu Ala Val Ser Leu Gly Glu Arg Ala
ACC CAG TCT CCA GAC TCC CTG GCT GTG TCT CTG GGC GAG AGG GCC 20                   25      27  27a 27b 27c 27d 27e 27f
Thr Ile Asn Cys Lys Ser Ser Gln Ser Val Leu Tyr Ser Ser Asn
ACC ATC AAC TGC AAG TCC AGC CAG AGT GTT TTA TAC AGC TCC AAC 30                       35                         40
Asn Lys Asn Tyr Leu Ala Trp Tyr Gln Gln Lys Pro Gly Gln Pro
AAT AAG AAC TAC TTA GCT TGG TAC CAG CAG AAA CCA GGA CAG CCT 45                       50                         55
Pro Lys Leu Leu Ile Tyr Trp Ala Ser Thr Arg Glu Ser Gly Val
CCT AAG CTG CTC ATT TAC TGG GCA TCT ACC CGG GAA TCC GGG GTC 60                       65                         70
Pro Asp Arg Phe Ser Gly Ser Gly Ser Gly Thr Asp Phe Thr Leu
CCT GAC CGA TTC AGT GGC AGC GGG TCT GGG ACA GAT TTC ACT CTC 75                       80                         85
Thr Ile Ser Ser Leu Gln Ala Glu Asp Val Ala Val Tyr Tyr Cys
ACC ATC AGC AGC CTG CAG GCT GAA GAT GTG GCA GTT TAT TAC TGT 90                       95                         100
Gln Gln Tyr Tyr Ser Thr Pro Pro Thr Phe Gly Gln Gly Thr Lys
CAG CAA TAT TAT AGT ACT CCT CCG ACG TTC GGC CAA GGG ACC AAG 105                      110
Val Glu Ile Lys Arg Thr Val Ala Ala Pro Ser Val Phe Ile Phe
GTG GAA ATC AAA CGA ACT GTG GCT GCA CCA TCT GTC TTC ATC TTC
```

Nucleotide and deduced amino acid sequence of the light chain of HuMab L612. Underlined amino acids represent the complementary determining regions CDR1, CDR2, and CDR3 in order.

FIG. 2

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 432 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens
( G ) CELL TYPE: Epstein Barr Virus Transformed B cell
( H ) CELL LINE: L612

( i x ) FEATURE:
( A ) NAME/KEY: CDS
( B ) LOCATION: 1..432
( D ) OTHER INFORMATION: /function="Heavy Chain"
/ product="Immunoglobulin Variable Region"
/ standardname="HuMab L612 Heavy Chain Variable Region Sequence"

( i x ) FEATURE:
( A ) NAME/KEY: miscfeature
( B ) LOCATION: 148..162
( D ) OTHER INFORMATION: /function="Complementary determining region 1 (CDR1)"

( i x ) FEATURE:
    ( A ) NAME/KEY: miscfeature
    ( B ) LOCATION: 271..300
    ( D ) OTHER INFORMATION: /function="Complementary
        determining region 2 (CDR2)"

( i x ) FEATURE:
    ( A ) NAME/KEY: miscfeature
    ( B ) LOCATION: 397..429
    ( D ) OTHER INFORMATION: /function="Complementary determining
        region 3 (CDR3)"

( x i ) SEQUENCE DESCRIPTION: SEQ ID NO:1:

```
ATG GAG TTT GGG CTG ACC TGG CTT TTT CTT GTG GCT AAT TTA AAA GGT     48
Met Glu Phe Gly Leu Thr Trp Leu Phe Leu Val Ala Asn Leu Lys Gly
 1               5                  10                  15

GTC CAG TGT GAG GTG CAG CTG TTG GAT TCT GGG GGA GGC TTG GTA CAG     96
Val Gln Cys Glu Val Gln Leu Leu Asp Ser Gly Gly Gly Leu Val Gln
                20                  25                  30

CCT GGG GGG TGC CTG AGA CTC TCC TGT GCA GCC TCT GGA TTC ACC TTT    144
Pro Gly Gly Cys Leu Arg Leu Ser Cys Ala Ala Ser Gly Phe Thr Phe
            35                  40                  45

AGC AGC TGT GCC ATG AGC TGG GTC CGC CAG GCT CCA GGG AAG GGG CTG    192
Ser Ser Cys Ala Met Ser Trp Val Arg Gln Ala Pro Gly Lys Gly Leu
        50                  55                  60

GAG TGG GTC TCA GCT ATT AGT GGT AGT GGT GGT AGC ACA TAC TAC GCA    240
Glu Trp Val Ser Ala Ile Ser Gly Ser Gly Gly Ser Thr Tyr Tyr Ala
 65                 70                  75                  80

GAC TCC GTG AAG GGC CGG TTC ACC ATC TCC AGA GAC AAA TCC AAG AAC    288
Asp Ser Val Lys Gly Arg Phe Thr Ile Ser Arg Asp Lys Ser Lys Asn
                85                  90                  95

ACG TTG TAT CTG CAA ATG AAC AGC CTG AGA GCC GAG GAC ACG GCC GTA    336
Thr Leu Tyr Leu Gln Met Asn Ser Leu Arg Ala Glu Asp Thr Ala Val
            100                 105                 110

TAT TAC TGT GCG AAA GGT GGC AAC GAT ATT TTG ACT GGT TAT TAT GCT    384
Tyr Tyr Cys Ala Lys Gly Gly Asn Asp Ile Leu Thr Gly Tyr Tyr Ala
        115                 120                 125

TGG GGC CAG GGA ACC CTG GTC ACC GTC TCC TCA GGG AGT GCA TCC GCC    432
Trp Gly Gln Gly Thr Leu Val Thr Val Ser Ser Gly Ser Ala Ser Ala
        130                 135                 140
```

( 2 ) INFORMATION FOR SEQ ID NO:2:

( i ) SEQUENCE CHARACTERISTICS:
        ( A ) LENGTH: 144 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Phe Gly Leu Thr Trp Leu Phe Leu Val Ala Asn Leu Lys Gly
 1               5                  10                  15

Val Gln Cys Glu Val Gln Leu Leu Asp Ser Gly Gly Gly Leu Val Gln
                20                  25                  30

Pro Gly Gly Cys Leu Arg Leu Ser Cys Ala Ala Ser Gly Phe Thr Phe
            35                  40                  45

Ser Ser Cys Ala Met Ser Trp Val Arg Gln Ala Pro Gly Lys Gly Leu
        50                  55                  60

Glu Trp Val Ser Ala Ile Ser Gly Ser Gly Gly Ser Thr Tyr Tyr Ala
 65                 70                  75                  80

Asp Ser Val Lys Gly Arg Phe Thr Ile Ser Arg Asp Lys Ser Lys Asn
                85                  90                  95
```

```
Thr Leu Tyr Leu Gln Met Asn Ser Leu Arg Ala Glu Asp Thr Ala Val
            100                 105                 110

Tyr Tyr Cys Ala Lys Gly Gly Asn Asp Ile Leu Thr Gly Tyr Tyr Ala
        115                 120                 125

Trp Gly Gln Gly Thr Leu Val Thr Val Ser Ser Gly Ser Ala Ser Ala
    130                 135                 140
```

( 2 ) INFORMATION FOR SEQ ID NO:3:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( C ) INDIVIDUAL ISOLATE: Epstein Barr Virus transformed B
            cell
        ( G ) CELL TYPE: B-cell
        ( H ) CELL LINE: L612

( i x ) FEATURE:
        ( A ) NAME/KEY: CDS
        ( B ) LOCATION: 1..360
        ( D ) OTHER INFORMATION: /function="Immunoglobulin light
            chain"
            / product="HuMab L612 Light Chain Variable Region"

( i x ) FEATURE:
        ( A ) NAME/KEY: miscfeature
        ( B ) LOCATION: 58..108
        ( D ) OTHER INFORMATION: /function="Complementary
            determining region 1 (CDR1)"

( i x ) FEATURE:
        ( A ) NAME/KEY: miscfeature
        ( B ) LOCATION: 154..174
        ( D ) OTHER INFORMATION: /function="Complementary
            determining region 2 (CDR2)"

( i x ) FEATURE:
        ( A ) NAME/KEY: miscfeature
        ( B ) LOCATION: 271..297
        ( D ) OTHER INFORMATION: /function="Complementary
            determining region 3 (CDR3)"

( x i ) SEQUENCE DESCRIPTION: SEQ ID NO:3:

```
ACC CAG TCT CCA GAC TCC CTG GCT GTG TCT CTG GGC GAG AGG GCC ACC      48
Thr Gln Ser Pro Asp Ser Leu Ala Val Ser Leu Gly Glu Arg Ala Thr
 1               5                  10                  15

ATC AAC TGC AAG TCC AGC CAG AGT GTT TTA TAC AGC TCC AAC AAT AAG      96
Ile Asn Cys Lys Ser Ser Gln Ser Val Leu Tyr Ser Ser Asn Asn Lys
             20                  25                  30

AAC TAC TTA GCT TGG TAC CAG CAG AAA CCA GGA CAG CCT CCT AAG CTG     144
Asn Tyr Leu Ala Trp Tyr Gln Gln Lys Pro Gly Gln Pro Pro Lys Leu
         35                  40                  45

CTC ATT TAC TGG GCA TCT ACC CGG GAA TCC GGG GTC CCT GAC CGA TTC     192
Leu Ile Tyr Trp Ala Ser Thr Arg Glu Ser Gly Val Pro Asp Arg Phe
     50                  55                  60

AGT GGC AGC GGG TCT GGG ACA GAT TTC ACT CTC ACC ATC AGC AGC CTG     240
Ser Gly Ser Gly Ser Gly Thr Asp Phe Thr Leu Thr Ile Ser Ser Leu
 65                  70                  75                  80

CAG GCT GAA GAT GTG GCA GTT TAT TAC TGT CAG CAA TAT TAT AGT ACT     288
Gln Ala Glu Asp Val Ala Val Tyr Tyr Cys Gln Gln Tyr Tyr Ser Thr
                 85                  90                  95
```

| CCT | CCG | ACG | TTC | GGC | CAA | GGG | ACC | AAG | GTG | GAA | ATC | AAA | CGA | ACT | GTG | 336 |
| Pro | Pro | Thr | Phe | Gly | Gln | Gly | Thr | Lys | Val | Glu | Ile | Lys | Arg | Thr | Val | |
| | | 100 | | | | | 105 | | | | | 110 | | | | |

| GCT | GCA | CCA | TCT | GTC | TTC | ATC | TTC | 360 |
| Ala | Ala | Pro | Ser | Val | Phe | Ile | Phe | |
| | | 115 | | | | 120 | | |

(2) INFORMATION FOR SEQ ID NO:4:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO:4:

| Thr | Gln | Ser | Pro | Asp | Ser | Leu | Ala | Val | Ser | Leu | Gly | Glu | Arg | Ala | Thr |
| 1 | | | | 5 | | | | | 10 | | | | | 15 | |

| Ile | Asn | Cys | Lys | Ser | Ser | Gln | Ser | Val | Leu | Tyr | Ser | Ser | Asn | Asn | Lys |
| | | | 20 | | | | | 25 | | | | | 30 | | |

| Asn | Tyr | Leu | Ala | Trp | Tyr | Gln | Gln | Lys | Pro | Gly | Gln | Pro | Pro | Lys | Leu |
| | | | 35 | | | | 40 | | | | | 45 | | | |

| Leu | Ile | Tyr | Trp | Ala | Ser | Thr | Arg | Glu | Ser | Gly | Val | Pro | Asp | Arg | Phe |
| | 50 | | | | | 55 | | | | | 60 | | | | |

| Ser | Gly | Ser | Gly | Ser | Gly | Thr | Asp | Phe | Thr | Leu | Thr | Ile | Ser | Ser | Leu |
| 65 | | | | | 70 | | | | | 75 | | | | | 80 |

| Gln | Ala | Glu | Asp | Val | Ala | Val | Tyr | Tyr | Cys | Gln | Gln | Tyr | Tyr | Ser | Thr |
| | | | | 85 | | | | | 90 | | | | | 95 | |

| Pro | Pro | Thr | Phe | Gly | Gln | Gly | Thr | Lys | Val | Glu | Ile | Lys | Arg | Thr | Val |
| | | | 100 | | | | | 105 | | | | | 110 | | |

| Ala | Ala | Pro | Ser | Val | Phe | Ile | Phe |
| | | 115 | | | | 120 | |

(2) INFORMATION FOR SEQ ID NO:5:

(i) SEQUENCE CHARACTERISTICS:
        (A) LENGTH: 38 nucleotides
        (B) TYPE: nucleic acid
        (C) STRANDEDNESS: single
        (D) TOPOLOGY: linear (ii) MOLECULE TYPE: oligonucleotide (iii) HYPOTHETICAL: NO (iv) ANTI-SENSE: NO (vi) ORIGINAL SOURCE:
        (A) ORGANISM:
        (C) INDIVIDUAL ISOLATE:
        (G) CELL TYPE:
        (H) CELL LINE:

(ix) FEATURE:
        (A) NAME/KEY:
        (B) LOCATION:
        (D) OTHER INFORMATION: Heavy Mu chain leader primer (xi) SEQUENCE DESCRIPTION: SEQ ID NO:5:

GGGAATTCAT GGACTGGACC TGGAGGAGTC CTTCTGTC    38

(2) INFORMATION FOR SEQ ID NO:6:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (i i) MOLECULE TYPE: oligonucleotide (i i i) HYPOTHETICAL: NO (i v) ANTI-SENSE: NO (v i) ORIGINAL SOURCE:
    (A) ORGANISM:
    (C) INDIVIDUAL ISOLATE:
    (G) CELL TYPE:
    (H) CELL LINE:

(i x) FEATURE:
    (A) NAME/KEY:
    (B) LOCATION:
    (D) OTHER INFORMATION: Heavy Mu chain leader primer (x i) SEQUENCE DESCRIPTION: SEQ ID NO:6:

GGGAATTCAT GGAGCTTTGG GCTGACGCTG GCGTTTCTT    39

(2) INFORMATION FOR SEQ ID NO:7:

(i) SEQUENCE CHARACTERISTICS:
        (A) LENGTH: 47 nucleotides
        (B) TYPE: nucleic acid
        (C) STRANDEDNESS: single
        (D) TOPOLOGY: linear (i i) MOLECULE TYPE: oligonucleotide (i i i) HYPOTHETICAL: NO (i v) ANTI-SENSE: NO (v i) ORIGINAL SOURCE:
    (A) ORGANISM:
    (C) INDIVIDUAL ISOLATE:
    (G) CELL TYPE:
    (H) CELL LINE:

(i x) FEATURE:
    (A) NAME/KEY:
    (B) LOCATION:
    (D) OTHER INFORMATION: Heavy Mu chain leader primer (x i) SEQUENCE DESCRIPTION: SEQ ID NO:7:

GGGAATTCAT GAGAACACAT ACTGTTGGTA TCGCATCTCG CTCTCTG    47

(2) INFORMATION FOR SEQ ID NO:8:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (i i) MOLECULE TYPE: oligonucleotide (i i i) HYPOTHETICAL: NO (i v) ANTI-SENSE: NO (v i) ORIGINAL SOURCE:
    (A) ORGANISM:
    (C) INDIVIDUAL ISOLATE:
    (G) CELL TYPE:
    (H) CELL LINE:

(i x) FEATURE:
    (A) NAME/KEY:
    (B) LOCATION:
    (D) OTHER INFORMATION: Heavy Mu chain J region primer (x i) SEQUENCE DESCRIPTION: SEQ ID NO:8:

CCAAGCTTAG ACGAGGGGGA AAAGGGTT    28

( 2 ) INFORMATION FOR SEQ ID NO:9:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE:
        ( G ) CELL TYPE:
        ( H ) CELL LINE:

( i x ) FEATURE:
        ( A ) NAME/KEY:
        ( B ) LOCATION:
        ( D ) OTHER INFORMATION: Light kappa chain leader primer ( x i ) SEQUENCE DESCRIPTION: SEQ ID NO:9:

GACATCGAGC TCACCCAGTC TCCA        24

( 2 ) INFORMATION FOR SEQ ID NO:10:

( i ) SEQUENCE CHARACTERISTICS:
        ( A ) LENGTH: 23 nucleotides
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE:
        ( G ) CELL TYPE:
        ( H ) CELL LINE:

( i x ) FEATURE:
        ( A ) NAME/KEY:
        ( B ) LOCATION:
        ( D ) OTHER INFORMATION: Light kappa chain leader primer ( x i ) SEQUENCE DESCRIPTION: SEQ ID NO:10:

GAAATTGAGC TCACGAGTCT CCA        23

( 2 ) INFORMATION FOR SEQ ID NO:11:

( i ) SEQUENCE CHARACTERISTICS:
        ( A ) LENGTH: 53 nucleotides
        ( B ) TYPE: nucleic acid
        ( C ) STRANDEDNESS: single
        ( D ) TOPOLOGY: linear ( i i ) MOLECULE TYPE: oligonucleotide ( i i i ) HYPOTHETICAL: NO ( i v ) ANTI-SENSE: NO ( v i ) ORIGINAL SOURCE:
        ( A ) ORGANISM:
        ( C ) INDIVIDUAL ISOLATE:
        ( G ) CELL TYPE:
        ( H ) CELL LINE:

( i x ) FEATURE:

(A) NAME/KEY:
(B) LOCATION:
(D) OTHER INFORMATION: Light kappa J region primer (xi) SEQUENCE DESCRIPTION: SEQ ID NO:11:

GCGCCGTCTA GAACTAACAC TCTCCCCTGT TGAAGCTCTT TGTGACGGGC AAG     53

HUMAN B-LYMPHOBLASTOID CELL LINE SECRETING ANTI-GANGLIOSIDE ANTIBODY

This is a continuation-in-part of patent application Ser. No. 07/609,803 which was filed on Nov. 5, 1990, now abandoned.

BACKGROUND OF THE INVENTION

This invention was made with Government support under Grant Nos. CA 30647, CA 42396 and CA 12582 awarded by the National Cancer Institute.

1. Field of the Invention

The present invention relates generally to Epstein-Barr virus-transformed human B-lymphoblastoid cell lines. More particularly, the present invention relates to such cell lines which are capable of producing antibodies which can be used to directly treat tumors or which can be used to raise anti-id antibodies for use as surrogate antigens or diagnostic reagents.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography. The contents of these publications and other reference materials are hereby incorporated by reference.

The possibility that the variable regions of immunoglobulins could act as external antigens was first recognized by Jerne in his idiotype network theory (1). According to this theory, recognition of idiotypes on the antigen-combining site, or on the framework of AB1, results in the production of anti-idiotypes (anti-ids or AB2) beta and alpha, respectively. Such "internal image" anti-idiotypes, by virtue of their complementarity with the original antigen binding site, mimic the original antigen and often behave in a similar biological manner. The concept of internal image refers to the fact that some AB2 molecules can act as surrogate antigens and their administration can lead to the production of anti-anti-idiotype antibodies displaying similar characteristics of AB1.

Immunization using anti-ids as surrogate antigens has generated much interest among researchers, many of whom have experimented with AB2 vaccines for active specific immunization against viruses, bacteria, and other pathogens (2,3). This approach is useful when a conventional vaccine or antibodies are not available, or are difficult to produce or when the corresponding antigen is not a suitable product for genetic engineering. In addition, anti-ids can be used as immunomodulators for up-regulating immunity against cancer, and as immunosuppressants to prevent rejection of transplanted organs and to prevent the progression of auto-immune disease.

Gangliosides are glycospingolipids that are fundamental membrane components on human tissues. Gangliosides undergo characteristic changes during malignant transformation of normal cells and thus are desirable target antigens for immunotherapy of cancer. Melanoma synthesizes a large number of gangliosides and thus has served as a useful model to assess the potential of gangliosides as immunotherapy targets. A number of tumor-associated gangliosides of human melanoma and their respective immonogenicity have been defined (12-29). In addition, a number of studies have shown that active immunization with ganglioside antigens results in prolonged survival of melanoma patients (4,5). Nevertheless, this technique suffers in many areas, namely that the ganglioside antigen are many times rare or in short supply.

Tumor-associated antigens, in most cases, are present in nature only at low levels and are relatively difficult to purify in large amounts. In contrast, anti-ids can be secreted from hybridoma cells at low cost over long periods of time. Furthermore, current genetic engineering technology, while not applicable to ganglioside epitopes, can be used to synthesize the anti-id peptides. Anti-ids previously developed for active specific immunotherapy of human cancer have used murine monoclonal antibodies (MuMabs) as the immunogens (6–11).

In addition to their use as surrogate antigens, murine monoclonal antibodies have also been employed to define and characterize many antigenic molecules on human cancer cells. Murine monoclonal antibodies have several advantages over human monoclonal antibodies including a strong affinity for tumor antigens, higher antibody secretion by hybridoma ascites, and high antigen density on tumor cells. However, with respect to therapeutic use, recent clinical trials with murine monoclonals have indicated that human monoclonal antibodies (HuMAbs) may be preferable since repeated injections of MuMAbs induce anti-murine Ig antibodies in virtually all patients. This leads to formation of immune complexes and immune reactions with potentially hazardous complications. In addition, HuMAbs may recognize epitopes that are overlooked by the murine immune system.

The development of HuMAbs that react with ganglioside antigens on human cancer cells and the demonstration of their anti-tumor effect at the clinical level has been reported (23,12). Patients with recurrent melanoma received intratumor injections of HuMAb to ganglioside GD2 or GM2, and partial or complete regression was observed in about 70% of the patients. In those melanoma patients in whom the immunotherapy was ineffective, the target antigen GD2 or GM2, was not expressed on the tumor cells. Two HuMAbs identified as L55 and L72 have been produced from human B-lymphoblastoid cell lines which have been transformed by Epstein-Barr virus (29). The L55 and L72 antibodies were both found to be reactive with a variety of tumor cells.

Because the quantity and quality of gangliosides on human melanoma are widely heterogeneous between different cancer patients, it is desirable to avoid unnecessary administration of HuMAb by examination of a pre-treatment biopsy to identify which gangliosides dominate on each patient's tumor cells.

There are three different immunological assays which have been used to detect the quality and quantity of gangliosides present on a given tumor. They include: the immune adherence assay (IA); direct immunofluorescence with fluorescinated microspheres; and IA absorption, and a biochemical assay. These assays each have certain limitations and advantages. The immunologic assay requires single cell suspensions from the biopsied tumor tissues. However, it is often difficult to obtain viable high yield tumor cell populations. Also, under a light microscope, tumor cells may not be readily distinguished from monocytes and macrophages. The biochemical assay does not require intact cells. However, a relatively large volume of tumor is necessary for ganglioside extraction and measurement of sialic acid in the glycolipid preparation.

The most commonly utilized immunologic technique for defining antigen expression on biopsy specimens using murine monoclonal antibodies is immunohistochemical staining of tissue sections. However, this sensitive method is not readily applicable to combinations of human monoclonal antibodies and human tissues. The indirect staining of human tumor tissues with the second antibody (anti-human Ig) usually results in high background from non-specific binding to abundant endogenous human Ig. Direct immunostaining using biotinylated human monoclonal antibodies may overcome this high background (30). However, this method is usually less sensitive and is most effective when a high density antigen is present on the cell surface.

There presently is a continuing need to develop additional human cell lines which are capable of producing antibody that is immunogenic with respect to the gangliosides present on tumors. The anti-ganglioside antibodies produced by the new cell lines will be useful in direct treatment of tumors and also in the production of anti-ids for use as surrogate antigens or diagnostic reagents.

SUMMARY OF THE INVENTION

In accordance with the present invention, a human B-lymphoblastoid cell line has been developed which secretes anti-ganglioside antibody which is reactive with a variety of tumors and which has been demonstrated to be effective in treating melanoma. The cell line of the present invention is identified as L612 and is maintained at the Division of Surgical Oncology at the University of California at Los Angeles School of Medicine. The L612 cell line was deposited on Apr. 4, 1991 at the American Type Culture Collection (Rockville, Md.) under ATCC accession number CRL 10724.

As a feature of the present invention, the L612 cell line is used to produce an IgM kappa antibody which is reactive with tumor antigen. The L612 antibody has been shown to be effective in treating melanoma tumors when administered by intralesional injection.

As another feature of the present invention, the L612 antibody is used to prepare murine anti-id monoclonal antibodies which are useful as surrogate antigens or which can be used in diagnostic procedures.

The above-described features along with many other features and attendant advantages of the present invention will become apparent as the invention becomes better understood by reference to the following detailed description.

SUMMARY OF THE DRAWINGS

FIG. 1 is the nucleotide/amino acid sequence for the variable region of the L612 antibody heavy chain. The complementary determining regions are underlined.

FIG. 2 is the nucleotide/amino acid sequence for the variable region of the L612 antibody light chain. The complementary determining regions are underlined.

DETAILED DESCRIPTION OF THE INVENTION

The cell line in accordance with the present invention is a B-lymphoblastoid cell line which has been transformed by the Epstein-Barr virus transformation technique. The cell line is identified as L612 and is maintained at the Division of Surgical Oncology at the University of California at Los Angeles School of Medicine. The L612 cell line was deposited on Apr. 4, 1991 at the American Type Culture Collection (12301 Parklawn Drive, Rockville, Md. 20852-1776) under ATCC accession number CRL 10724.

The L612 cell line was established in culture from lymphocytes by the same Epstein-Barr virus transformation technique which was used to produce two other human monoclonal anti-ganglioside antibodies, L55 (anti-GM2) and L72 (anti-GD2) (26-27 and 29). The same transformation procedure as set forth in detail in reference (29) was followed in establishing the L612 cell line. The Epstein-Barr virus transformation technique used to establish the prior L55 and L72 cell lines, as well as the present L612 cell line, is a conventional procedure which is known and used by researchers in this field.

The specific procedure which was used to establish the L612 cell line is as follows.

Regional lymph nodes were received from a patient with breast cancer during mastectomy. Lymphocytes were separated from these lymph nodes by first cutting the lymph nodes into small pieces and suspending them in Hank's balanced salt solution (HBSS). The suspension was then passed through a stainless mesh to separate large tissue blocks, and centrifuged on Ficoll density gradient solution to condense and separate the lymphocytes. The E-rosette formation technique was used to remove T-lymphocytes, and the B-lymphocyte fraction was washed with HBSS three times and then were incubated with Epstein-Barr virus (EBV) for 20 hours in RPMI 1640 containing 10% fetal calf serum. Cells were cloned by the limiting dilution technique and monitored for antibody production by the IA assay as described previously. (29).

A human breast cancer cell line, MDA-MB 436 (31) and a human melanoma cell line, UCLA-SO-M12 (32) were used as targets. While clones secreting antibodies positive to 436 breast cancer cell line ceased to produce antibodies very soon after establishment, those reacting to the M12 melanoma cell line continued to produce antibody and were stable. Clones secreting antibodies were adapted to RPMI 1640 containing a lower concentration of fetal calf serum gradually. The clones were then recloned 7 times in serum free medium containing growth factor (FDA approved HB series serum free medium obtained from Irvine Scientific Co.) (Irvine, Calif.). Doubling time of L612 cell line is less than one day. The cell line secretes greater than 20 $\mu$g/ml IgM kappa monoclonal antibody. The L612 antibody in the spent medium was purified as previously described (25). In addition, the antibody produced by the L612 cell line is isolated according to any of the conventional procedures used to remove and purify antibodies from cell cultures.

The purified L612 antibody was tested for reactivity with a variety of human tumor tissues. The L612 antibody has a strong cytotoxic activity to antigen positive human tumor cells in the presence of complement. The reactivity was tested using both the immune adherence (IA) and immune adherence absorption (IAA) assays. The results are summarized in TABLE I.

TABLE I

| Reactivity of L612 to Human Cancer and Non-cancer Tissues. | | |
|---|---|---|
| | #positive/ #tested | Specimens Relative antigenicity* |
| Biopsied Tissues | | |

TABLE I-continued

Reactivity of L612 to Human Cancer and Non-cancer Tissues.

|  | #positive/<br>#tested | Specimens<br>Relative anti-<br>genicity* |
|---|---|---|
| Melanoma | 13/21** | +++ |
| Peripheral Blood Cells |  |  |
| Lymphocytes | 0/32** | — |
| Erythrocytes | 0/44** | — |
| Cultured cell lines |  |  |
| Melanoma | 12/16 | +++ |
| Lung | 4/4 | ++ |
| Breast | 5/7 | + |
| Gastro-intestine | 2/7 | + |
| Erythroleukemia | 0/1 | — |
| T-Cell leukemia | 1/1 | + |
| Myeloma | 0/1 | — |
| Neuroblastoma | 0/1 | — |
| B-lymphoblasts*** | 0/11** | — |

*In the direct IA assay a partially purified HuMAB L612 (0.116 Ag µg IgM/ml) was used.
**These tissues were tested by the IA absorption assay.
***These were derived from Epstein-Barr virus transformed peripheral blood lymphocytes of melanoma patients.

A total of 21 biopsied melanoma, peripheral blood lymphocytes (PBLs) from 32 different donor and erythrocytes from an additional 44 donors were tested. Thirteen of 21 melanoma tissues (62%) were antigen positive in contract, none of PBLs (0/32) and erythrocytes (0/44) were positive. Cultured human malignant cell lines also were investigated for the presence of the antigen (Table 1). Of 16 melanoma cell lines tested by the direct IA assay, 12 (75%) were positive. Positive reactivity of other cancer cell lines were as follows: lung cancer, 4/4; breast cancer, 5/7; gastro-intestinal cancer, 2/7; other types of cancer, 1/4. However, none of eleven Epstein-Barr virus transformed B-cell lines autologous to the melanoma cell lines tested were positive even by the sensitive IA absorption technique. Though the percent positive specimens of melanoma was lower than that of lung cancer, overall reactivity per specimen was much higher in melanoma than other histologic type of cancer. Of the melanoma cell lines tested M15 and M12 showed the highest reactivity. Treatment of the cells with neuraminidase completely abolished the antigenicity of the cell lines while treatment with trypsin did not.

The reactivity of the L612 antibody with various authentic glycolipids was also determined. The glycolipids and their respective antigen titer with respect to L612 antibody are listed in Table II.

TABLE II

|  | Antigen Titer |
|---|---|
| Neutral Glycolipid |  |
| GbOse$_3$-Cer (CTH) | 0 |
| GbOse$_4$-Cer (Globoside) | 0 |
| GgOse$_4$-Cer (Asialo-GM$_1$) | 0 |
| Gangliosides |  |
| I$^3$NeuAc-Gal-Cer (GM$_4$) | 64 |
| II$^3$NeuAc-Lac-Cer (GM$_3$) | 64 |
| II$^3$NeuGc-Lac-Cer (GM$_3$) | 0 |
| II$^3$NeuAc-GgOse$_3$-Cer (GM$_2$) | 0 |
| II$^3$NeuAc-GgOse$_4$-Cer (GM$_2$) (GM$_{1a}$) | 0 |
| IV$^3$NeuAc-nLcOse$_4$-Cer (SPG) | 16 |
| IV$^3$NeuGc-nLcOse$_4$-Cer | 0 |
| II$^3$NeuAc$_2$-Lac-Cer (GD$_3$) | 0 |
| II$^3$NeuAc$_2$-GgOse$_3$-Cer (GD$_2$) | 0 |
| IV$^3$NeuAc—,II$^3$NeuAc-GgAc-GgOse$_4$-Cer (GD$_{1a}$) | 0 |
| II$^3$NeuAc$_2$-GgOse$_4$-Cer (GD$_{1b}$) | 0 |
| IV$^3$NeuAc—, II$^3$NeuAc$_2$-GgOse$_4$-Cer (GT$_{1b}$) | 0 |

The authentic glycolipids (5 nmol), were tested for L612 antigen activity by the IA inhibition test. Three gangliosides, GM$_4$, GM$_3$ and PSG showed positive reactivity; however, two of these, GM$_4$ and GM$_3$ showed stronger binding (1:64) than SPG (1:16). Other gangliosides including II$^3$NeuGc-Lac-Cer, IV$^3$NeuGc-nLcOse$_4$-Cer, GM$_2$, GM$_{1a}$, GD$_3$, GD$_2$, GD$_{1a}$, GD$_{1b}$ and GT$_{1b}$, and neutral glycolipids including GbOse$_3$-Cer, GbOse$_4$-Cer and GgOse$_4$-Cer showed no antigenic activity. To further confirm the above results, ELISA and enzyme immunostaining on TLC plates with authentic glycolipids were performed. The results obtained by ELISA and enzyme immunostaining were similar to those of the IA inhibition assay. The ELISA was performed using 15 authentic glycolipids bound to microtiter wells. Again, the three gangliosides, GM$_3$, GM$_4$ and SPG showed clear binding activity on solid phase ELISA. None of the remaining glycolipids showed reactivity.

Enzyme immunostaining of TLC plates with GM4, GM3, SPG, GD3, GD2, GM2, N-glycoryl GM3, CDH, globoside and asialo GM1 (lug) was also performed. Strong positivity was shown with GM3 and GM4. Milder reactivity was observed with SPG. Very faint reactivity was observed with GM2. Other glycolipids failed to be stained. Results of these three different types of immunologic assays demonstrate that HuMAb L612 detects the terminal sugar of gangliosides, such as GM3 and GM4, which have a NeuAc α2-3 Galactose residue.

Immunostaining of frozen sections with HuMab L612 indicated a strong specificity for neoplastic tissue, including melanoma, colon adenocarcinomas and lung adenocarcinomas. HuMab provides an excellent marker for identifying certain types of neoplastic tissues. It has been shown that HuMab L6 12 binds to renal cell carcinomas (35).

The DNA sequence of the variable regions for both the light and heavy chains of the L612 antibody were determined by polymerase chain reaction (PCR). The guanidium thiocyanate/cesium chloride procedure was used to prepare total RNA from the L612 B lymphoblast line (34). Ten µg of RNA was mixed with 60 pmol of either mu heavy or kappa light chain 3' primers and heated at 70° C. for 10 min. The mixture was then added to 50 µl reverse transcriptase reaction solution containing 10 µl 5X reverse transcriptase buffer (BRL), 4 µl 10 mM dNTP mix (200 µM of dATP, dCTP, dGTP, and dTTP final concentration) and 3 µl 600 units reverse transcriptase (Superscript, BRL). The mixture was incubated at 37° C. for 1 hour.

A Standard PCR reaction was then performed with: 97 µl of PCR mixture was added to 3 µl of RNA-cDNA mixture. The PCR mixture contained 10X pCR buffer (Perkin Elmer, Calif.), 10 mM dNTPs mix at 60 µM final concentration of each dNTP, 5 units of Taq polymerase (Perkin Elmer), and 60 µM appropriate 5' and 3' heavy and light chain primers. The mixtures were subjected to 35 cycles of amplification at 91° C. for 1 in., 52° C. for 2 min., and 72° C. for 1.5 min. followed by a final incubation at 72° C. for 10 min. in a Perkin Elmer/Cetus thermal cycler. An aliquot of the PCR product was on a 2% agarose gel to verify the correct size band product. The mu heavy chain and kappa light chain primers produced a 495 and 603 base pair cDNA product, respectively. When the gel showed a correct size single product the remainder of the PCR-cDNA product was subjected to PCR to obtain more product.

The gel products were isolated, pooled, subjected to phenol/chloroform extraction and ethanol precipitation. The DNA was then digested with appropriate restriction enzymes, extracted, precipitated and purified with GeneClean (Bio101, CA). The DNA was ligated into appropriate cut restriction sites of Bluescript vector (Stratagene, Calif.). Ten independent clones of the variable region mu chain and four independent clones of the variable region kappa chain were isolated and sequenced. A $J_H$ heavy chain probe was used for screening and verifying the heavy chain clones. Sequencing was done by the dideoxynucleotide method with T7 DNA polymerase (Sequenase, USB, Cleveland, Ohio) according to the manufacturer's protocol. The primers used were as follows. Heavy mu chain leader primers (3 primers) (29):
GGGAATTCATGGACTGGACCTGGAGG-(AG)TC(CT)TCT(GT)C Sequence No. 5;
GGGAATTCATGGAG(CT)TTGGGCT-GA(CG)CTGG(CG)TTT(CT)T Sequence No. 6; and
GGGAATTCATG(AG)A(AC)(AC)(AT-)ACT(GT)TG(GT)(AT)(CG)-C(AT)(CT)(CG)CT(CT)CTG Sequence No. 7. This contains an EcoRI (underlined) restriction site to facilitate cloning. Heavy mu chain J region primer was CCAAGCTTAGACGAGGG-GGAAAAGGGTT Sequence No. 8. This contains an Hind III site (underlined). Light kappa chain leader primers were as follows (2 primers)(30). GA-CATCGAGCTCACCCAGTCTCCA Sequence No. 9; and GAAAT TGAGCTCACGAGTCTCCA Sequence No. 10. These primers contain an Sac I site (underlined). The light kappa chain J region primer was GCGCCGTCTAGAAC-TAACACTCTCCCCTGTTGAAGCTCTTTGT-GACGGGCAAG Sequence No. 11. This primer contains an Xba site (underlined).

The cloned cDNA nucleotide sequence and the encoded amino acid sequence for the variable region of the heavy chain is set forth in SEQ ID NO:1. The heavy chain variable region amino acid sequence above is set forth in SEQ ID NO: 2. The cloned cDNA nucleotide sequence and the encoded amino acid sequence for the variable region of the light chain is set forth in SEQ ID NO:3. The light chain variable region amino acid sequence above is set forth in SEQ ID NO:4.

The nucleotide/amino acid sequence for the heavy chain variable region is also shown in FIG. 1. The complimentary determining regions (CDR's) 1, 2 and 3 are underlined. The nucleotide/amino acid sequence for the light chain variable region is also shown in FIG. 2. The CDR's 1, 2 and 3 are also underlined.

The L612 antibody in accordance with the present invention is administered to patients for treating tumors which contain the GM3 ganglioside or NeuAc2-3 Galactose epitope. The GM3 ganglioside includes a terminal sugar having a Neuα2-3 Galactose residue. Any of the conventional procedures used for administering antibodies to patients for treating such tissues may be used. These procedures include intravenous or intraperitoneally injection and intralesional injection. Intralesional injection is a preferred method of administration for cutaneous recurrent tumors. The L612 antibody and the antibody producing cell line can be modified or altered by known procedures to form other immunoglobulin isotypes and cells producing such which may efficiently bind and kill tumor cells (33). The particular dosage used will vary depending upon tumor antigenicity and can be determined according to known procedures for administering antibodies such as L55 and L72. The L612 monoclonal antibody reacts strongly with human melanoma tumor biopsies. The L612 antibody also reacts less strongly with human tumor biopsies from lung cancer, breast cancer, pancreatic cancer, colon cancer and kidney cancer. The UCLASO-M12 melanoma cell line was identified as the most reactive cell line among the lines tested with the L612 monoclonal antibody. The UCLASO-M12 cell line is maintained at the Division of Surgical Oncology at the University of California at Los Angeles School of Medicine.

L612 HuMab was used as therapeutic agent for the treatment of cutaneous malignant melanoma. HuMab L612 was purified for human use as previously described (25). It was demonstrated in previous studies that intralesional injection of human anti-$G_{D2}$ HuMab L72 could induce regression of cutaneous melanoma (23). In the present example the effect of HuMab L612 and HuMab L72 is compared.

The 84 year old female underwent surgical excision of a rapidly growing cutaneous melanoma lesion (1.9×1.6 cm) on her left cheek. Pathological examination of the tissue section revealed a melanoma of Clark's level IV. The ganglioside expression of the lesion biopsy was found to be moderately positive for $G_{M3}$ and negative for $G_{D2}$. Two weeks after surgery, a recurrence developed at the incision site. The upper lesions were treated weekly with 1 ml HuMab L612, and the lower lesions were treated with 1 ml HuMab L72 HuMab. After treatment for one month (3 treatments), necrosis and softening of lesions treated with HuMab L612 were observed. In contrast treated with HuMab L72 HuMab showed no response, and in fact, had further progressed. The patient eventually expired due to extensive metastases in the liver and brain.

The L612 antibody is also useful in producing hybridomas which in turn can be used to produce anti-ids for use as surrogate antigens or diagnostic reagents. The production of hybridomas and subsequent generation of anti-ids are described in the following exemplary procedure:

BALB/c mice were immunized by a subcutaneous injection of 200 μg of purified L612 monoclonal antibody in complete Freund's adjuvant. After 2 weeks the animals were boosted by another subcutaneous injection of L612 in incomplete Freund's adjuvant. Eleven days following the booster, the mice were injected intraperitoneally with 200 μg of L612 in saline. After three days the spleens were removed and the splenocytes fused with myeloma cell line SP2/O using the standard procedure to produce hybridomas.

After HAT medium selection, hybridoma culture wells were tested for antibody using ELISA. Hybridomas secreting anti-ids (AB2) were identified by their strong binding reactivity to HuMAb L612 and absent reactivity to three other control human IgMs: L55, L72, and human serum IgM. Unrelated proteins used as antigens included fetal bovine serum and human serum albumin. 50 μl of IgMs or proteins (50 μg/ml) were coated on a 96-well ELISA plate and served as antigens to detect AB2. Peroxidase-conjugated goat anti-mouse IgG+IgM was used as the AB2 detection probe followed by substrate and reading absorbency at 490 nm as described previously (19).

HAT selection of approximately 2500 hybridoma culture wells which were prepared as described above yielded 40 hybridomas secreting antibodies with distinct reactivity to L612 HuMAb, but no reactivity to three other control human IgMs and two unrelated serum protein antigens. To determine whether these anti-L612 antibodies were AB2 beta-type directed against the antigen combining site of L612, or were AB2 alpha antibodies bound to peptide regions outside the antigen-combining site of L612, the inhibitory activity of these anti-L612 antibodies against L612 binding to GM3 positive target cell lines or to the purified antigen, ganglioside GM3, was tested by using three assay systems: IA inhibition, cell-ELISA inhibition, and GM3-ELISA inhibition. Of the 40 antibodies tested, seven inhibited L612 binding to an antigen positive target melanoma cell line, (UCLASO-M12), and to GM3 greater than 50% in the assays, while 12 others had weak or no inhibitory activity.

Of the seven inhibitory anti-ids, one identified as 4C10 was selected for cloning as the preferred beta-type anti-id for use in treating tumors. From the non-inhibitory group the anti-id identified as 18C6 was selected for cloning as the preferred alpha-type anti-id for use in immunodiagnostic assays. Both anti-ids, 4C10 and 18C6, were tested with isotype antiglobulins and found to be of the IgG1 class and contain kappa light chains.

The 4C10 and 18C6 cloned hybridoma cell lines were grown in FCS-containing RP MI 1640 medium and secreted 5–10 μg/ml of antibody into culture supernatants. Titers of the anti-ids in these culture supernatants against L612 by ELISA ranged between 1:200 to 1:1000/$10^6$ hybridoma. Anti-id 18C6 demonstrated low binding inhibition of HuMAb L612 to target cells in the IA assay and to ganglioside GM3 in ELISA whereas 4C10 at the same antibody concentration showed strong inhibition in both the ELISA assay and the IA assay. As a control assay, 4C10 and 18C6 failed to inhibit the binding of an unrelated antigen system, HuMAb L72, to M14 target cells, or to GD2 antigen. The lack of binding inhibition of 18C6 indicates a binding location on L612 antibody outside the GM3 antigen combining site, and the specific binding inhibition of 4C10 indicates its binding location to be within or near the antigen combining site.

The hybridoma cell lines which secrete the 4C10 and 18C6 monoclonal anti-ids are being maintained at the Division of Surgical Oncology at the University of California at Los Angeles School of Medicine.

The 4C10 anti-id and other beta-type anti-ids raised against L612 can be used alone or in combination with other agents to treat tumors. They are preferred for use in treating melanoma tumors. These beta-type anti-ids may also be used as an immunomodulator to enhance anti-cancer immunity, suppress organ transplant rejection and suppress autoimmune disease.

The beta-anti-ids may be administered by any of the conventional procedures used to introduce antibodies into patients. These procedures include subcutaneous, intravenous or intratumor injection. The beta-type anti-ids are preferably conjugated with KLH and emulsified in a suitable carrier such as Freund's complete adjuvant. The particular doses used for the beta-type anti-ids will vary depending upon the tumor being treated and numerous other factors. The dosage levels are established by the known techniques and principles generally recognized and utilized in treating patients with antigen immunization agents or monoclonal antibodies.

The immunogenic usefulness of the beta-type anti-ids to L612 antibody was demonstrated as follows:

Five syngeneic Balb/c mice were immunized with purified 4C10-KLH. As controls, four mice were immunized with mouse IgG1-KLH and one mouse with KLH alone. The immunized sera were monitored by ELISA using purified GM3 as the antigen source and by the IA assay using the antigen positive M12 melanoma cell line. In the ELISA, peroxidase conjugated goat anti-mouse IgM+IgG (Boeringer Mannheim) was used as a second antibody.

Measurable antibody (AB3) was produced in three of the five immunizations with 100 μg 4C10-KLH. The immunized sera bound to GM3 but not to CDH (asialo-GM3). Sera from the five mice immunized with IgG-KLH or KLH alone gave no response to either glycolipid. In further analysis to determine the Ig class of the AB3 (ELISA and TLC immunostaining), the majority of the reactivity was identified as IgM.

In order to exclude the species specific natural antibodies that might react to M12 cells in the IA assay, the immunized murine sera were pre-absorbed by human red blood cells at 4° C. overnight. An IA score of 4+ was obtained at 1:10 dilution of the absorbed sera. Control sera gave no reactivity even at 1:2 dilution. To confirm that the positive reactivity was directed against GM3 antigen on the cell surface, IA inhibition was performed using GM3 (10 μg), CDH (10 μg), 4C10 (10 μg) and unrelated IgG1 (10 μg) purified from Balb/c hybridoma ascites. While reactivity was completely inhibited by GM3 or purified 4C10, no inhibition was obtained with CDH or unrelated IgG1.

The above example demonstrates that beta-type anti-ids produce AB3 anti-bodies which are immunoreactive with melanoma tumors. Accordingly, these beta-type anti-ids which are raised in response to the L612 antibody are effective as an immunization agent in the treatment of melanoma.

The alpha-type anti-ids produced in response to the L612 antibody may be used immunodiagnostic procedures such as a three-step cell-ELISA procedure and a three step immunoperoxidase staining of tumor tissue sections. Examples of practice are as follows:

Three-step cell-ELISA

Viable M12 cells ($1 \times 10^5$) were plated onto a U-bottom 960 well microtiter plate (Immulon-1, Dynatec) after pre-blocking with 1% BSA-PBS. 50 ul of L612 (100 μg/ml) were added and incubated for 1 hour at room temperature. After washing the mixture to remove unbound HuMAb L612, the cells were incubated with murine monoclonal anti-id 18C6 (100 μg/ml) for 1 hour at room temperature. After washing, 50 μl of peroxidase-conjugated goat anti-mouse IgG antibody (1/10,000 diluted) (Jackson Immuno Research) were added and the plate was incubated for 30 minutes. After washing with PBS solution, the substrate for peroxidase was added and binding activity was determined as a function of absorbance at 490 nm with a $V_{max}$ kinetic microplate reader.

When the antigen combining sites of L612 are occupied by GM3 expressed on tumor cells, the cell bound HuMAb L612 should have reduced its binding activity to anti-id beta, yet still retain full binding activity to anti-id alpha. The above-described procedure confirmed this process using cultured M12 melanoma cells which express a high density of the corresponding antigen.

The above-described cell binding assay represents a modified form of the ELISA technique. Several control assays were included to establish the specificity of the positive reaction. Control anti-ganglioside HuMAbs included L55 (IgM anti-GM2) and L72 (IgM anti-GD2), both of which exhibit strong binding ability to the GM2 and GD2 rich M14 melanoma cell line (26, 27). The anti-id 18C6 reacted strongly to M12 cells after pre-incubation with HuMaB L612, but did not react to M14 cells that were pre-incubated with L55 or L72 HuMAb. The peroxidase-conjugated anti-mouse Ig also failed to react with M12 cells in other controls including murine anti-id alone, L612, or L612 plus (anti-id beta).

The cell-ELISA assay was then applied to several other human tumor cell lines. A two-step cell binding assay (HuMAb+peroxidase-conjugated anti-human IgM) was compared with the three-step cell-binding assay to evaluate the validity of the three-step assay. The three-step assay had parallel reactivity with the two-step assay and was slightly more sensitive in almost every cell line. This data indicates that the ELISA absorbency value of the three-step assay accurately reflects differences in the density of cell surface GM3 antigens and correlates closely with the two-step in vitro assays.

Three-step Immunoperoxidase Staining of Tissue Sections

Tissue sections 4 μm thick were cut from tissues freshly frozen in OTC compound and immediately fixed in cold formaldehyde buffer (12 g Tris buffer, 9 g sodium chloride, 40 ml 37% formaldehyde, pH 7.4) and air dried. Slides were dipped in Tris buffer for five minutes then treated with 3% hydrogen peroxide for 10 minutes to quench endogenous peroxidase activity.

After washing in running water for five minutes, sections were overlaid with 5% normal human serum for 20 minutes. HuMAb L612 (10 μg IgM in 200 μl) was then applied and incubated for 45 minutes. The slides were washed in Tris buffer for 5 minutes, the purified anti-id 18C6 (10 μg IgG1 in 200 ul) was applied and incubated for 30 minutes.

After washing the slides again, the third antibody, a biotinylated goat anti-mouse IgG (Vector Laboratories, Burlingame, Calif.) at 1/100 dilution was applied and incubated for 25 minutes. Peroxidase-conjugated streptavidin (1/1000 dilution) (Zymed Laboratories, San Francisco) was added after washing and incubated for 20 minutes. After washing, the slides were immersed in substrate solution containing 6 ml amino-ethyl carbazole, 50 ml of 0.02M sodium acetate buffer (pH 5.1), and 0.4 ml of freshly prepared 3% hydrogen oxide for 5 minutes. The slides were washed once more in tap water, counterstained with hematoxylin, and cover-slips applied to the stained sections using glycerol-gelatin. The immunoperoxidase three-step assay was applied successfully to detect binding of L612 antibody to surgically biopsied tumor tissues that had been snap frozen.

Having thus described exemplary embodiments of the present invention, it should be noted by those skilled in the art that the within disclosures are exemplary only and that various other alternatives, adaptations and modifications may be made within the scope of the present invention. For example, the L612 antibody may be used to make chimeric antibodies which are also useful in a variety of treatments or as diagnostic reagents. Accordingly, the present invention is not limited to the specific embodiments as illustrated herein, but is only limited by the following claims.

BIBLIOGRAPHY

1. Jerne NK. Towards a network theory of the immune system. Ann Immunol (Paris) 125C: 373–389, 1974.
2. Dalgleish AG, Kennedy RC. Anti-idiotype antibodies as immunogens: idiotype-based vaccines. Vaccine 6: 215–220, 1962.
3. Sikorska HM. Therapeutic applications of anti-idiotypic antibodies. J Biol Res Mod 7: 327–358, 1988.
4. Livingston PO, Natoli EJ, Calves MJ, Stockert E, Oettgen HF, Old LJ. Vaccines containing purified GM2 ganglioside elicit GM2 antibodies in melanoma patients. Proc Natl Acad Sci USA 84: 2911–2915, 1987.
5. Livingston PO. Experimental and clinical studies with active specific immunotherapy. In "Immunity to Cancer II." Eds MS Mitchell, Pub Alan L Liss, Inc, NY.
6. Herlyn D, Wettendorff M, Schmoll E. Anti-idiotype immunization of cancer patients: modulation of immune response. Proc Natl Acad Sci 84: 8055–8059, 1987.
7. Bhattacharya-Chatterjee M, Pride MW, Seon BK, Kohler H. Idiotype vaccines against human T-cell acute lymphoblastic leukemia. I. Generation and characterization of biologically active monoclonal anti-idiotypes. J Immunol 139: 1354–1360, 1987.
8. Viale G, Grassi F, Pelagi M, Alzani R, Menard S, Miotti S, Buffa R, Gina A, Siccardi AG. Anti-human tumor antibodies induced in mice and rabbits by "internal image" anti-idiotype monoclonal immunoglobulins. J Immunol 139: 4250–4255, 1987.
9. Chen H, Mittelman A, Yamada M. Association of restricted specificity of anti-anti-idiotypic antibodies with prolonged survival of melanoma patients. Proc Amer Assoc Clin Oncol 8: A1125, 1989.
10. Kahn M, Hellstrom I, Estin CD, Hellstrom KE. Monoclonal anti-idiotypic antibodies related to the p97 melanoma antigen. Cancer Res 49: 3157–3162, 1989.
11. Barth A, Waibel R, Stahei RA. Monoclonal anti-idiotypic antibody mimicking a tumor-associated sialoglycoprotein antigen induces humoral immune response against human small cell lung carcinoma. Int J Cancer 43: 896–900, 1989.
12. Irie RF, Matsuki T, Morton DL. Human monoclonal antibody to ganglioside GM2 for melanoma treatment. Lancet 1: 786–787, 1989.
13. Tsuchida T, Saxton RE, Morton DL, Irie RF. Gangliosides of human melanoma II. Cancer, 623: 1166–1174, 1989.
14. Ravindranath MH, Morton DL, Irie RF. An epitope common to ganglioside O-acetyl AD3 recognized by antibodies in melanoma patients after active specific immunotherapy. Cancer Res 49: 3691–3897, 1989.
15. Hoon DBS, Ando I, Sviland G, Tsuchida T, Okun E, Morton DL, Irie RF. Ganglioside GM2 expression on human melanoma cells correlates with sensitivity to lymphokine-activated killer cells. Int J Cancer 43: 857–862, 1989.
16. Hoon DBS, Irie RF, Cochran AJ. Gangliosides from human melanoma immodulate response of T-cells to interleukin-2. Cell Immunol 111: 410–419, 1988.
17. Ravindranath MH, Paulson JC, Irie RF. Human melanoma antigen O-acetylated ganglioside GD3 is 17. recognized by cancer autennarius lectin.1 J Biol Chem 263: 2079-2086, 1988.
18. Tsuchida T, Ravindranath MH, Saxton RE, Irie RF. Gangliosides of human melanoma: Altered expression in vivo and in vitro. Cancer Res 47: 1278-1281, 1987.
19. Tai T, Sze LL, Kawashima I, Saxton RE, Irie RF. Monoclonal antibody detects monosialoganglioside having sialic acid 2-3 Galactosyl residue. J Biol Chem 262: 6803-6807, 1987.
20. Ando I, Hoon DSB, Suzuki Y, Saxton RE, Golub SH, Irie RF. Ganglioside GM2 on the K56 cell line is recognized as a target structure by human natural killer cells. Int J Cancer 40: 12-17, 1987.
21. Tsuchida T, Saxton RE, Irie RF. Gangliosides of human melanoma: GM2 and tumorigenicity. J Natl Cancer Inst 78: 55-60, 1987.
22. Tsuchida T, Saxton RE, Morton DL, Irie RF. Gangliosides of human melanoma. J Natl Cancer Inst 78: 45-54, 1987.
23. Irie RF, Morton DL. Regression of cutaneous metastatic melanoma by intralesional injection with human monoclonal antibody to ganglioside GD2. Proc Natl Acad Sci 83: 8694-8698, 1986.
24. Katano M, Irie RF. Suppressed growth of human melanoma in nude mice by human monoclonal antibody to ganglioside GD2. Immunology Letters 8: 169-174, 1984.
25. Katano M, Saxton RE, Irie RF. Human monoclonal antibody to tumor-associated ganglioside GD2. J Clin Lab Immunol 15: 119-126, 1984.
26. Tai T, Paulson JC, Cahan LD, Irie RF. Ganglioside GM2 as a human tumor antigen (OFA-I-1). Proc Natl Acad Sci, USA 80: 5392-5396, 1983.
27. Cahan LD, Irie RF, Singh R, Cassidenti A, Paulson JC. Identification of human neuroectodermal tumor antigen (OFA-I-1) as ganglioside GD2. Proc Natl Acad Sci 79: 7629-7633, 1982.
28. Tai T, Cahan LD, Tsuchida T, Saxton RE, Irie RF, Morton DL. Immunogenicity of melanoma-associated gangliosides in cancer patients. Int J Cancer 35: 607-612, 1985.
29. Irie RF, Sze L1, Saxton RE. Human antibody to OFA-I, tumor antigen produced in vitro by EBV-transformed human B-lymphoblastoic cell lines. Proc Natl Acad Sci 79: 5666-5670, 1982.
30. Yano T, Yasumoto K, Nagashima A, Murakami H, Hashizume S and Nomoto K (1988) Immunohistological characterization of human monoclonal antibody against lung cancer. J Surg Oncol. 39, 108.
31. Higuchi, M, DS Robinson, R Cailleau, RF Irie, and DL Morton. 1980. A serologic study of cultured breast cancer cell lines: lack of antibody response to tumour specific membrane antigens in patients. *Clin. Exp. Immunol.* 39: 90.
32. Irie RF, Irie K, and Morton DL. 1976. A membrane antigen common to human cancer and fetal brain tissue. *Cancer Res.* 36: 3510.
33. Steplewski, et al., Proceedings of the National Academy of Sciences, U.S.A., 82: 8653, 1985.
34. Chromczynski P, and Sacchi N. 1987. Single-step method of RNA isolation by acid quanidinium thiocyanate-phenol-chloroform extraction. Anal. Biochem. 162: 156-159.
35. Hoon, DSB., Okun E, Banez M, Irie RF, and Morton DL. 1991. Interleukin-4 alone and gamma interferon or α-tumor necrosis factor inhibits cell growth and modulates cell surface antigens on human renal cell carcinomas. Cancer Res. 51: 5687-5693.

What is claimed is:

1. A human B-lymphoblastoid cell line which is identified as L612 and which is deposited at the American Type Culture Collection under ATCC accession number CRL 10724.

2. A composition of matter comprising an anti-ganglioside antibody which is secreted by the L612 human B-lymphoblastoid cell line and isotypes thereof.

3. A method for treating melanoma containing gangliosides comprising the step of treating said melanoma with an immunoeffective amount of L612 antibody.

4. A method for treating melanoma according to claim 3 wherein said melanoma comprises tumor tissue containing gangliosides.

5. A composition of matter according to claim 2 wherein said composition of matter consists essentially of said antibody and a pharmaceutically acceptable carrier.

6. A method for treating a melanoma patient having tumor tissues containing gangliosides, said method comprising the step of administering to said patient a pharmaceutically effective amount of the composition according to claim 5.

7. A method for treating a melanoma patient according to claim 6 wherein said composition is administered by intralesional injection.

8. A composition of matter comprising an antibody which is secreted by the L612 human B-lymphoblastoid cell line and isotypes thereof wherein said antibody comprises a heavy chain variable region comprising the amino acid sequence set forth in SEQ ID NO: 2.

9. A composition of matter comprising an antibody which is secreted by the L612 human B-lymphoblastoid cell line and isotypes thereof wherein said antibody comprises a light chain variable region comprising the amino acid sequence set forth in SEQ ID NO: 4.

10. A composition of matter according to claim 8 wherein said antibody comprises a light chain variable region comprising the amino acid sequence set forth in SEQ ID NO: 4.

11. A composition of matter comprising an antibody which is secreted by the L612 human B-lymphoblastoid cell line and isotypes thereof wherein said antibody comprises a heavy chain variable region comprising complementary determining regions as set forth in SEQ ID NO: 1.

12. A composition of matter comprising an antibody which is secreted by the L612 human B-lymphoblastoid cell line and isotypes thereof wherein said antibody comprises a light chain variable region comprising complementary determining regions as set forth in SEQ ID NO: 1.

13. A composition of matter according to claim 12 said antibody which is secreted by the L612 human B-lymphoblastoid cell line and isotypes thereof wherein said antibody comprises a light chain variable region comprising complementary determining regions as set forth in SEQ ID NO: 4.

* * * * *